(12) United States Patent
Lui

(10) Patent No.: US 8,617,191 B2
(45) Date of Patent: Dec. 31, 2013

(54) PROBE COUPLER ASSEMBLY

(75) Inventor: Chun Kee Lui, Monroeville, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/474,075

(22) Filed: May 17, 2012

(65) Prior Publication Data

US 2012/0253368 A1    Oct. 4, 2012

Related U.S. Application Data

(62) Division of application No. 12/028,381, filed on Feb. 8, 2008, now Pat. No. 8,202,284.

(60) Provisional application No. 60/901,422, filed on Feb. 15, 2007.

(51) Int. Cl.
*A61B 17/08* (2006.01)

(52) U.S. Cl.
USPC .......................................................... 606/153

(58) Field of Classification Search
None
See application file for complete search history.

(56) References Cited

U.S. PATENT DOCUMENTS

| | | | | |
|---|---|---|---|---|
| 3,240,207 A | * | 3/1966 | Barker et al. | 600/488 |
| 4,419,999 A | * | 12/1983 | May et al. | 600/504 |
| 4,607,637 A | * | 8/1986 | Berggren et al. | 606/153 |
| 4,624,257 A | * | 11/1986 | Berggren et al. | 606/153 |
| 4,790,325 A | * | 12/1988 | Lee | 600/490 |
| 4,917,090 A | * | 4/1990 | Berggren et al. | 606/153 |
| 4,917,091 A | * | 4/1990 | Berggren et al. | 606/153 |
| 4,926,875 A | * | 5/1990 | Rabinovitz et al. | 600/504 |
| 4,997,439 A | * | 3/1991 | Chen | 606/216 |
| 5,022,410 A | * | 6/1991 | Hall et al. | 600/454 |
| 5,123,908 A | * | 6/1992 | Chen | 606/153 |
| 5,250,057 A | * | 10/1993 | Chen | 606/153 |
| 5,289,821 A | * | 3/1994 | Swartz | 600/455 |
| 5,336,233 A | * | 8/1994 | Chen | 606/153 |
| 5,588,436 A | | 12/1996 | Narayanan et al. | 128/662.03 |
| 6,077,227 A | * | 6/2000 | Miesel et al. | 600/486 |
| 6,254,618 B1 | * | 7/2001 | Dakov | 606/153 |
| 6,277,078 B1 | | 8/2001 | Porat et al. | 600/486 |
| 6,716,169 B2 | * | 4/2004 | Muramatsu et al. | 600/443 |
| 7,192,400 B2 | * | 3/2007 | Campbell et al. | 600/486 |
| 2004/0082868 A1 | * | 4/2004 | Campbell et al. | 600/504 |
| 2005/0055022 A1 | * | 3/2005 | Schubert | 606/49 |

FOREIGN PATENT DOCUMENTS

| | | |
|---|---|---|
| WO | WO 01/97695 A1 | 12/2001 |
| WO | WO 2006/102020 A2 | 9/2006 |

OTHER PUBLICATIONS

International Search Report and Written Opinion dated Jun. 13, 2008, from International Application No. PCT/US2008/053428 (13 pgs.).

* cited by examiner

*Primary Examiner* — Corrine M McDermott
*Assistant Examiner* — Son Dang
(74) *Attorney, Agent, or Firm* — Brinks Gilson & Lione

(57) ABSTRACT

An assembly for joining two vessel segments of a patient includes a coupler formed of adjoining coupler halves. Each coupler half includes an aperture for receiving an end of one of the vessel segments. One of the coupler halves includes a connector element configured for connection to the other coupler half. The vessel segments are alignable in the respective coupler halves such that a path for fluid flow is formed therebetween upon connection of the coupler halves. A probe is aligned in engagement with a coupler half for generating a signal corresponding to fluid flow through the path.

11 Claims, 2 Drawing Sheets

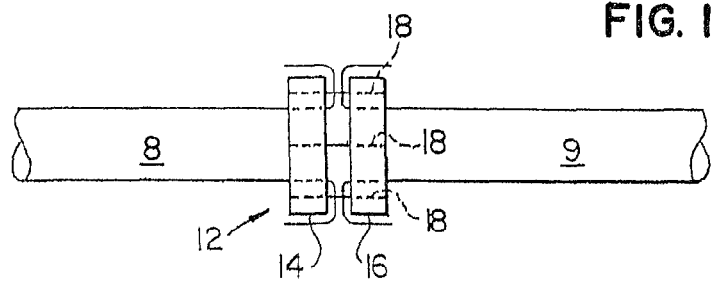
FIG. 1
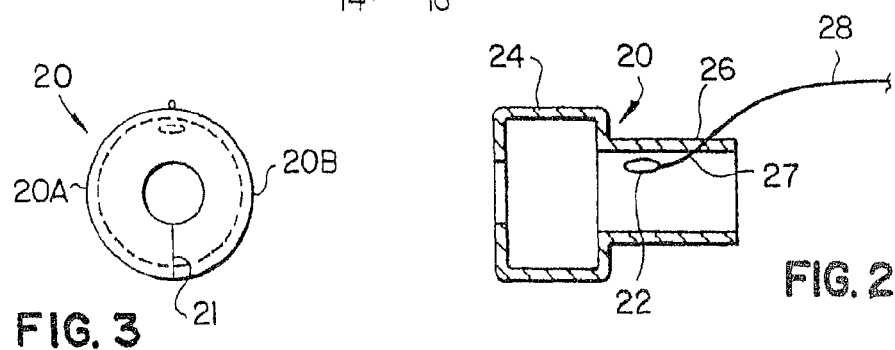
FIG. 2
FIG. 3
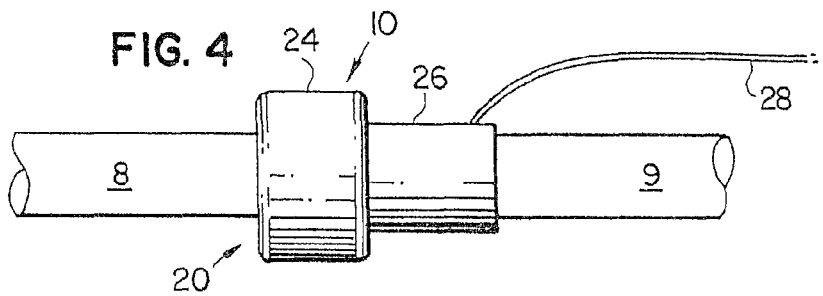
FIG. 4
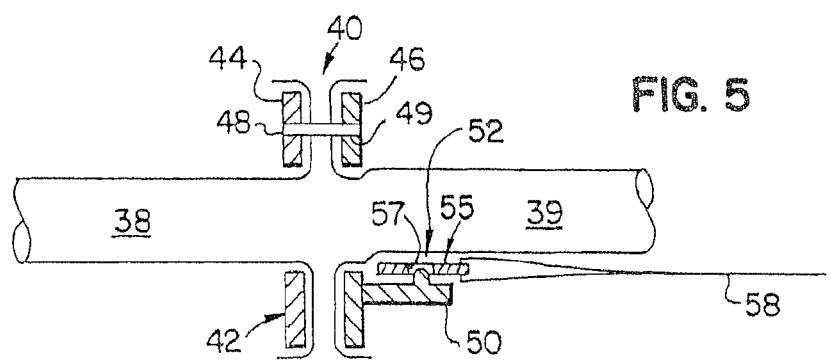
FIG. 5
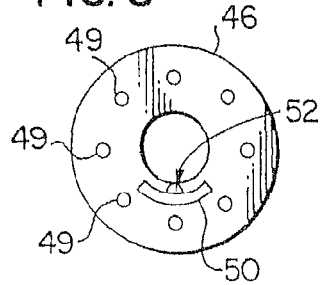
FIG. 6
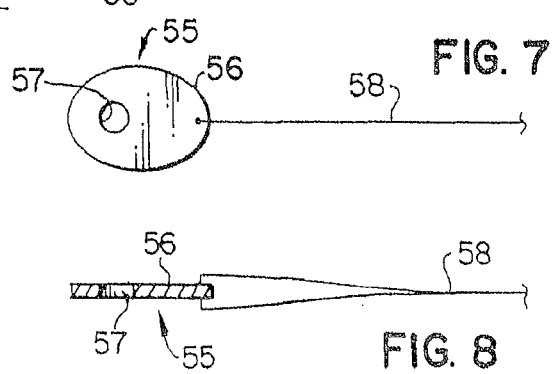
FIG. 7
FIG. 8

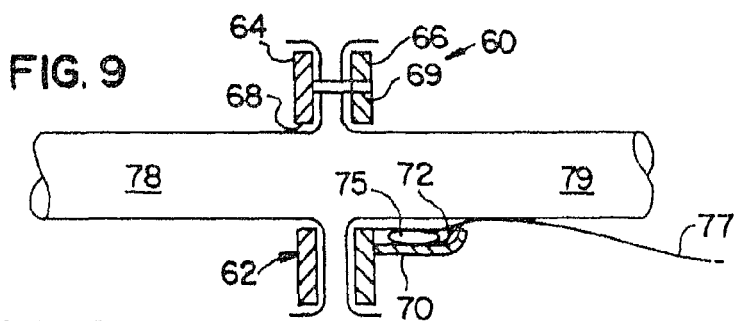
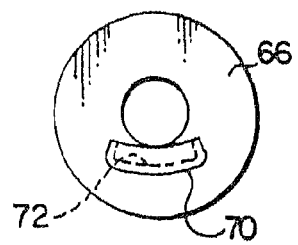
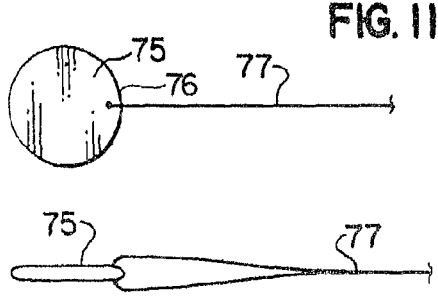
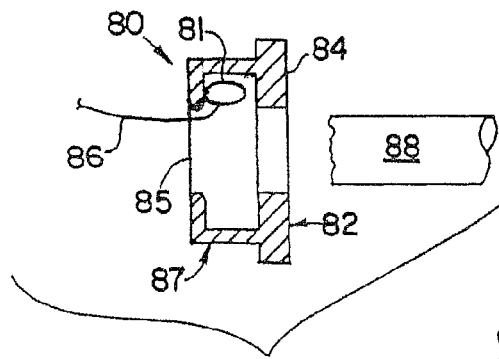
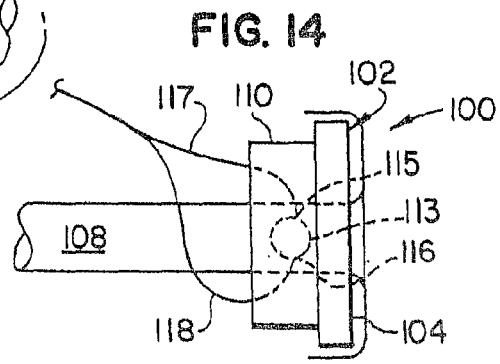
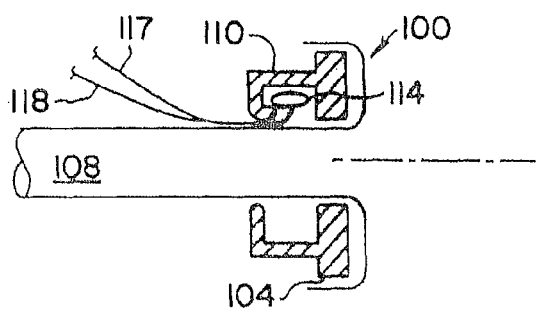
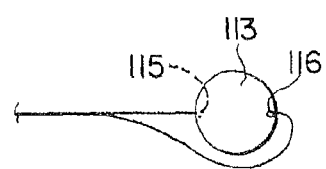

PROBE COUPLER ASSEMBLY

RELATED APPLICATION

The present patent document is a divisional of prior U.S. patent application Ser. No. 12/028,381, filed Feb. 8, 2008, now U.S. Pat. No. 8,202,284, entitled PROBE COUPLER ASSEMBLY, and further claims the priority and benefit of the filing date under 35 U.S.C. 119(e) of provisional U.S. patent application Ser. No. 60/901,422, filed Feb. 15, 2007, both of which are hereby incorporated by reference.

BACKGROUND

1. Technical Field

This application relates to a coupling device. More particularly, the application relates to a device for coupling segments of body vessels, and monitoring the flow of fluid through the coupled vessel.

2. Background Information

A variety of microvascular surgical procedures have been developed in recent years which have markedly improved the quality of life for the affected patients. Such procedures include, among others, reconstructive surgery following free tissue transfer, organ transfer surgery, and coronary artery bypass graft (CABG) procedures.

Free tissue transfer entails the removal of tissue and/or muscle from one part of the body, along with an associated artery and vein, and reattachment of the tissue and/or muscle to another part of the body. The artery and vein of the transferred tissue and/or muscle are then anastomosed (i.e., connected) to a native artery and vein to achieve blood circulation in the transferred tissue and/or muscle. Typically, an anastomotic coupling device is provided for this connection. With this type of device, each one of the vessels is incorporated into a separate half of the coupling device, and the halves are thereafter anastomosed to provide leak-free joinder of the respective vessels.

Once a microvascular surgical technique has been carried out, the attached vessel should be monitored for a period of time to insure that blood continues to flow through the vessel. One device utilized to monitor such flow is the Cook-Swartz Doppler Flow Probe and Monitor System. This System utilizes an implantable probe inserted in a cuff. The cuff is wrapped around the vessel, slightly downstream from the site of joinder, in a manner such that the probe is in intimate contact with the vessel. When properly aligned, the probe provides a signal corresponding to fluid flow through the vessel. Lack of a signal alerts medical personnel that fluid flow has reduced to an unacceptable level, and that intervention is required. Once the signal has been received for a designated period of time, such as a few days to a week, the probe may be removed.

Following removal of the probe, the cuff may be surgically removed, or in most cases, simply left in position around the vessel. Surgical removal requires that an incision be made in the patient's skin of sufficient size to allow withdrawal of the cuff. An incision of this size causes discomfort to the patient, and involves subjecting the patient to an additional surgical procedure very shortly after the tissue transfer or other anastomotic procedure.

It would be desirable to combine the probe with the anastomotic coupling device, in a manner such that installation of a separate coupling device and probe is not necessary, and in a manner such that a satisfactory signal may be achieved through the probe.

BRIEF SUMMARY

The shortcomings of the prior art are addressed by the features of the present invention.

In one form thereof, the invention comprises an assembly for joining two vessel segments of a patient. The assembly comprises a coupler comprising adjoining coupler halves, and a cuff having a large diameter portion and a small diameter portion. Each of the coupler halves includes an aperture for receiving an end of one of the vessel segments. One of the coupler halves comprises a connector element sized and shaped for connection to the other coupler half. The vessel segments are alignable in the respective coupler halves such that a path for fluid flow is formed therebetween upon connection of the coupler halves. The large diameter portion of the cuff is positioned over at least a portion of the coupler, and the small diameter portion of the cuff is positioned over one of the vessel segments. The cuff further includes a probe positioned at the small diameter portion. The probe is positioned within the cuff such that a signal is receivable therein corresponding to fluid flow through the vessel segment.

In another form thereof, the invention comprises an assembly for joining two vessel segments of a patient comprising a coupler having adjoining coupler halves, and a probe. Each coupler half comprises an aperture for receiving an end of one of the vessel segments. One of the coupler halves comprises a connector element sized and shaped for connection to the other coupler half. The vessel segments are alignable in the respective coupler halves such that a path for fluid flow is formed therebetween upon connection of the coupler halves. One of the coupler halves includes an extension member extending axially therefrom. The probe is positioned in the extension member in a manner such that a signal is generated corresponding to fluid flow through the path.

In yet another form thereof, the invention also comprises an assembly for joining two vessel segments of a patient. The assembly comprises a coupler comprising adjoining coupler halves, and a probe. Each of the coupler halves comprises an aperture for receiving an end of one of the vessel segments. One of the coupler halves comprises a connector element sized and shaped for connection to the other coupler half. The vessel segments are aligned in the respective coupler halves such that a path for fluid flow is formed therebetween upon connection of the coupler halves. One of the coupler halves includes a generally circumferential cavity extending axially therefrom. The probe is received in the cavity and positionable therein for generating a signal corresponding to fluid flow through the path.

BRIEF DESCRIPTION OF THE DRAWINGS

FIG. 1 is a side view illustrating an anastomotic coupler of a type that may be utilized in the inventive assembly;

FIG. 2 is a side sectional view of a cuff of a type that may be utilized in the inventive assembly;

FIG. 3 is an end view of the cuff of FIG. 2;

FIG. 4 is a side view of the inventive probe/coupler assembly;

FIG. 5 is side view of another embodiment of a probe/coupler assembly according to the present invention, showing the coupler in section;

FIG. 6 is an end view of the coupler of FIG. 5;

FIG. 7 is a top view of a probe that may be used in connection with the coupler of FIG. 5;

FIG. 8 illustrates a side sectional view of the probe of FIG. 7;

FIG. 9 is side view of another embodiment of a probe/coupler assembly according to the present invention, showing the coupler in section;

FIG. 10 is an end view of the coupler of FIG. 9;

FIG. 11 is a top view of a probe that may be used in connection with the coupler of FIG. 9;

FIG. 12 illustrates a side view of the probe of FIG. 11;

FIG. 13 illustrates a side sectional view of another embodiment of a coupler;

FIG. 14 is a side view of a probe/coupler assembly according to yet another alternative embodiment;

FIG. 15 is a side sectional view of the coupler of the assembly of FIG. 14;

FIG. 16 is a side view of the probe of the embodiment of FIG. 14;

FIG. 17 is a top view of the probe of the embodiment of FIG. 14;

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated assembly, and such further applications of the principles of the invention as illustrated therein being contemplated as would normally occur to one skilled in the art to which the invention relates.

In the following discussion, the terms "proximal" and "distal" will be used to describe the opposing axial ends of the inventive assembly, as well as the axial ends of various components of the assembly. The term "proximal" is used in its conventional sense to refer to the end of the assembly (or component thereof) that is closest to the operator during use of the assembly. The term "distal" is used in its conventional sense to refer to the end of the assembly (or component thereof) that is initially inserted into the patient, or that is closest to the patient.

FIGS. 1-4 illustrate a probe/coupler assembly 10, and components thereof, according to one embodiment of the present invention. As best shown in FIG. 4, probe/coupler assembly 10 is used to anastomose two body vessel segments, such as veins 8, 9, to provide free blood flow therebetween. Probe/coupler assembly 10 includes an anastomotic coupler 12 and a cuff 20. Cuff 20 includes a probe 22, such as a Doppler probe, suitable for detecting fluid flow through the joined vessel segments.

Anastomotic coupler 12 includes coupler halves 14, 16. Coupler halves 14, 16 may be of conventional design, and may have a generally cylindrical configuration. Preferably, coupler halves 14, 16 are fabricated from polyethylene, PTFE, nitinol, or other long-term implantable material, and each coupler half is provided with a central aperture therethrough. The apertures are available in various sizes such that an end of each one of veins 8, 9 (which typically range from about 1 to 3 cm in diameter), may be received through the aperture in a respective coupler half. One of the coupler halves 14, 16 includes connector elements, and the other coupler half includes structure for receiving the connector elements. In the embodiment shown, the connector elements comprise a series of axially directed connector pins 18 spaced along the circumference of coupler half 16 that are receivable, such as by a threaded connection, in corresponding apertures (not shown) in the mating coupler half 14. When connector pins 18 are received in the corresponding apertures in the opposing coupler half, the coupler halves 14, 16 are maintained in the relative positions shown in FIG. 1. As a result of this connection, the ends of the vessel segments are joined, thereby establishing fluid flow communication between respective vein segments 8, 9. Coupling devices of this general configuration are known in the art, and further description of them is not necessary for an understanding of the present invention.

FIG. 2 illustrates a sectional view of cuff 20. Cuff 20 is typically made of an elastic material, such as silicone or polyurethane, by conventional procedures such as injection molding. The crystal of the probe may be affixed to the inside of the cuff with a small amount of an adhesive. Suitable probes are commercially available, such as the Cook-Swartz Doppler Flow Probe, available from Cook Incorporated, of Bloomington, Ind. In the embodiment shown, cuff 20 includes a large diameter portion 24 and a small diameter portion 26. Large diameter portion 24 has an inner diameter the same as, or slightly larger than, the outer diameter of assembled coupler halves 14, 16. Smaller diameter portion 26 has an inner diameter the same as, or slightly larger than, the outer diameter of vein segment 9. Cuff 20 further includes probe 22, such as a Doppler crystal, installed along smaller diameter portion 26. A pair of probe wires 28 extend from the crystal to connect probe 22 to a conventional receiving unit in well known fashion. One example of a suitable receiving unit is the Cook-Swartz Blood Flow Monitor, also available from Cook Incorporated, of Bloomington, Ind. In the embodiment shown, probe wires 28 extend through an aperture 27 formed in the smaller diameter portion 26 to the receiving unit.

Preferably, cuff 20 is provided with a slit 21 (FIG. 3) extending through one wall of the cuff. Cuff halves 20A and 20B may be pivoted open at slit 21, and the cuff may be positioned over the coupler and the vein. The elasticity of the cuff will generally be sufficient to enable it to spring back into the closed position shown in FIG. 3 following installation. When properly positioned, the crystal is positioned so that it contacts or is otherwise in close contact with the vein segment 9. For optimal signal pickup, the crystal should be in intimate contact with the blood vessel. Those skilled in the art will appreciate, however, that other arrangements are possible that are also capable of acceptable signal pickup. If desired, a coupling agent, such as a gel (as described hereinafter), may be applied to enhance signal pickup. The Doppler monitor may be turned on during the probe implant procedure to determine if the signal pickup is adequate.

Another embodiment of coupler 42 for use in a probe/coupler assembly 40 is illustrated in FIG. 5. Coupler 42, comprising coupler halves 44, 46, is provided to anastomose body vessel segments, such as veins 38, 39. One or more connector elements, such as connector pin 48, extend from one coupler half, in this case coupler half 44. Connector pin 48 is received in a receptacle, such as aperture 49, in the other coupler half, in this case coupler half 46. If desired, a plurality of axially directed connector pins 48 may be spaced along the circumference of coupler half 44, and a corresponding plurality of apertures 49 may be provided to receive the connector pins, in the manner shown in FIG. 1.

An arc-shaped extension 50 extends axially from a surface of coupler half 46. Extension 50 is sized such that when the coupler is assembled as shown in FIG. 5, the extension is spaced approximately 0.5 mm from vein 39. Extension 50 is best shown in FIG. 6. A protuberance 52 extends radially from the inner arc portion of extension 50. If desired, arc 50 and protuberance 52 may be formed from the same composition as the coupler halves.

FIG. 7 illustrates a top view of a probe 55 that may be used in connection with coupler 42 to form a probe/coupler assembly 40. FIG. 8 illustrates a side view of the probe of FIG. 7. Probe 55 includes a crystal 56, and can be formed to have any conventional shape. However, in this instance, probe 55 is provided with an aperture 57 extending through the probe. When coupler 40 is assembled as shown in FIG. 5, probe 55 may be inserted between arc-shaped extension 50 and vein 39 as illustrated. Probe aperture 57 is sized such that when probe 55 is inserted as described, protuberance 52 is received in aperture 57. Protuberance 52 extends radially approximately 0.5 mm from the inner surface of arc-shaped extension 50. As a result, probe 55 is securely received and held in position by protuberance 52.

When properly aligned, the probe crystal comes into intimate contact with vein 39. In this way, there is no signal loss resulting from transmission of the signal through the coupler. Furthermore, there is no signal diffraction going through the coupler. Preferably, however, protuberance 52 extends only a distance necessary to securely hold probe 55 in position as described, but not such a distance that the probe 55 cannot be easily removed. In this instance, probe 55 may be detached from coupler 42 by simply pulling laterally on probe wires 58. Preferably, protuberance 52 and aperture 57 are provided with corresponding gently curved surfaces to facilitate detachment in this manner.

FIG. 9 illustrates another embodiment of a probe/coupler assembly 60. Assembly 60 comprises a coupler 62 similar in many respects to coupler 42 of FIG. 5. Coupler 62 includes coupler halves 64, 66 that are provided to anastomose body vessel segments, such as veins 78, 79. One or more connector elements, such as connector pin 68, extend from one coupler half, in this case, coupler half 64. Connector pin 68 is received in a receptacle, such as aperture 69, in the other coupler half, in this case coupler half 66. As with the previous embodiments, if desired a plurality of axially directed connector pins 68 may be spaced along the circumference of coupler half 64, and a corresponding plurality of apertures 69 may be provided to receive the connector pins.

Coupler 62 also includes a generally arc-shaped extension 70 that extends axially from a surface of coupler half 66. Unlike the protuberance that is provided in extension 50 of FIG. 5, arc-shaped extension 70 is configured to provide a pocket for receiving a probe 75. Extension 70 is sized such that when the coupler is assembled as shown in FIG. 5, the extension is spaced approximately 0.5 mm from vein 39. Those skilled in the art will appreciate that alternate spacings may be acceptable for providing a sufficient signal in some instances.

FIG. 11 illustrates a top view of a probe 75 that may be used in connection with coupler 62 to form a probe/coupler assembly 60. FIG. 12 illustrates a side view of the probe of FIG. 11. Probe 75 includes a crystal 76, and can be formed to have any conventional shape. Similarly, the pocket of extension 70 can be formed to have any complementary shape for receiving probe 75. Probe wires 77 extend from the crystal in conventional fashion. However, in this instance, probe 75 need not have a central aperture extending therethrough as in probe 55. When coupler 60 is assembled as shown in FIG. 9, probe 75 may be inserted into pocket 72 between arc-shaped extension 70 and vein 79 as illustrated. The depth of pocket 72 is preferably gauged such that crystal 76 is in intimate contact with vein 79.

FIG. 13 illustrates a variation of the embodiment of FIGS. 9-12. In this embodiment, rather than providing a pocket to receive the probe, probe/coupler assembly 80 includes a coupler 82 having a circumferential capturing cavity 87 axially extending from coupler half 84 for receiving probe 81. Preferably, capturing cavity 87 is sized to snugly receive probe 81 therein, such that probe is positioned in intimate contact with vein 88. Only one half 84 of coupler 82 is illustrated in FIG. 13. Probe wires 86 extend to a receiving unit through an aperture 85 in the capturing cavity.

FIGS. 14-17 illustrate still another variation of a probe/coupler assembly 100. In this embodiment, assembly 100 includes coupler 102 as before, one-half 104 of which is shown in FIGS. 14 and 15. The other half of coupler 102 and a cuff similar to cuff 24 in FIG. 1 are not shown in these figures. Vein 108 extends through an aperture in coupler half 104. This embodiment includes a capturing cavity 110, similar to that of FIG. 13. A probe 114 is captured between vein 108 and cavity 110. As shown in FIGS. 16 and 17, crystal 113 is arranged in a manner such that the joints 115, 116 between probe wires 117, 118 and the probe crystal do not interfere with the capturing cavity. By placing the joints at diametrically opposite edges of the crystal, and by aligning the joints in the circumferential direction in the cavity, a lower overall profile can be achieved.

When a probe is utilized to measure fluid flow through an anastomosed vessel, it is known that good signal transmission can be achieved if the piezoelectric crystal is positioned directly on the blood vessel, or as close to the vessel as is practicable. Typically, either a flexible cuff or a rigid coupler is utilized to achieve such positioning. On some occasions, such as when the crystal is placed in a pocket or cavity of the coupler, it is not possible to achieve direct positioning. In these cases, the signal transmission between the crystal and the blood vessel can be problematic, as the signal must pass through all the different layers of material between the crystal and the blood vessel.

When a void or air pocket exists between two layers of material, signal transmission can be impaired. In the present assembly, air pockets between the cavity or pocket and the probe can be purged by introducing a gel or gel-like substance into the cavity or pocket prior to installing the probe. Alternatively, the crystal may be coated with the gel prior to inserting it into the cavity or pocket. Silicone gel and various collagen compositions are non-limiting examples of suitable materials may be introduced into the cavity or pocket to purge air pockets. Such materials typically provide good acoustic coupling for the crystal. Preferably only small amounts of the gel are used, and the gel is not so absorbent or reflective as to cause a significant reduction of the signal. As an alternative to the use of a gel, a saline solution may be added into the cavity or pocket. However, although suitable for purging air pockets, those skilled in the art will appreciate that saline may not be as easy to retain in the cavity or pocket as a gel.

It is therefore intended that the foregoing detailed description be regarded as illustrative rather than limiting, and that it be understood that it is the following claims, including all equivalents, that are intended to define the spirit and scope of this invention.

The invention claimed is:

1. An assembly for joining two vessel segments of a patient, comprising:
 a coupler comprising adjoining coupler halves, each of said coupler halves comprising an aperture for receiving an end of one of said vessel segments, one of said coupler halves comprising a connector element sized and shaped for connection to the other coupler half, said vessel segments alignable in said respective coupler halves such that a path for fluid flow is formed therebetween upon connection of said coupler halves; and a cuff having a large diameter portion and a small diameter portion, said large diameter portion positioned over at least a portion of each of said coupler halves, said small diameter portion positioned such that one of said vessel segments extends therethrough when said vessel segments are aligned in said respective coupler halves, said cuff further comprising a probe positioned at said small diameter portion, said probe positioned within said cuff such that a signal is receivable therein corresponding to fluid flow through said one vessel segment.

2. The assembly of claim 1, wherein said connector element comprises at least one connector pin projecting from a surface of said coupler half in a direction of said other coupler half, said other coupler half comprising a receptacle for said connector pin.

3. The assembly of claim 1, wherein said connector element comprises a plurality of axially directed connector pins spaced along a circumference of said coupler half in a direction of said other coupler half, and wherein said other coupler half comprises a plurality of receptacles for receiving respective connector pins.

4. The assembly of claim 1, wherein said cuff is formed of an elastic material.

5. The assembly of claim 4, wherein said elastic material comprises silicone or polyurethane.

6. The assembly of claim 4, wherein a wall of said cuff has a slit formed therethrough in a manner such that said cuff may be pivoted to an open position to facilitate positioning of said cuff around said coupler.

7. The assembly of claim 1, wherein said coupler halves are formed from polyethylene, PTFE or nitinol.

8. The assembly of claim 1, wherein said probe is affixed to an inside surface of said cuff small diameter portion.

9. An assembly for joining two vessel segments of a patient, comprising:

a coupler comprising adjoining coupler halves, each of said coupler halves comprising an aperture for receiving an end of one of said vessel segments, one of said coupler halves comprising a connector element sized and shaped for connection to the other coupler half, said vessel segments alignable in said respective coupler halves such that a path for fluid flow is formed therebetween upon connection of said coupler halves; and a cuff having a large diameter portion and a small diameter portion, said large diameter portion positioned over at least a portion of said coupler, said small diameter portion positioned over one of said vessel segments, said cuff further comprising a probe positioned at said small diameter portion, said probe positioned within said cuff such that a signal is receivable therein corresponding to fluid flow through said one vessel segment, wherein a wall of said cuff has a slit formed therethrough in a manner such that said cuff may be pivoted to an open position to facilitate positioning of said cuff around said coupler.

10. The assembly of claim 9, wherein said connector element comprises a plurality of axially directed connector pins spaced along a circumference of said coupler half in a direction of said other coupler half, and wherein said other coupler half comprises a plurality of receptacles for receiving respective connector pins.

11. The assembly of claim 9, wherein said probe is affixed to an inside surface of said cuff small diameter portion.

* * * * *